United States Patent [19]

Whittam et al.

[11] 4,101,598

[45] Jul. 18, 1978

[54] ISOMERIZATION OF ALKYL BENZENES USING A NU-1 ZEOLITE CATALYST

[75] Inventors: Thomas Vincent Whittam, Stockton-on-Tees; Barry Youll, Middlesbrough, both of England

[73] Assignee: Imperial Chemical Industries Limited, London, England

[21] Appl. No.: 828,827

[22] Filed: Aug. 29, 1977

Related U.S. Application Data

[62] Division of Ser. No. 727,773, Sep. 29, 1976, Pat. No. 4,060,590.

[30] Foreign Application Priority Data

Oct. 3, 1975 [GB] United Kingdom ............... 40631/75
Feb. 9, 1976 [GB] United Kingdom ................ 4957/76
Jul. 29, 1976 [GB] United Kingdom ............... 31641/76

[51] Int. Cl.$^2$ .............................................. C07C 15/08
[52] U.S. Cl. ............................. 260/668 A; 260/672 T
[58] Field of Search ..................... 260/668 A, 672 T

[56] References Cited

U.S. PATENT DOCUMENTS

3,948,758  4/1976  Bonacci et al. ................ 260/668 A
4,060,590  11/1977  Whittam et al. ...................... 423/328

*Primary Examiner*—Delbert E. Gantz
*Assistant Examiner*—C. E. Spresser
*Attorney, Agent, or Firm*—Cushman, Darby & Cushman

[57] ABSTRACT

A process for the isomerization of xylenes using the hydrogen form of new zeolite "nu-1" having a silica to alumina ratio of 20 to 150 and a characteristic X-ray diffraction pattern and adsorption properties.

3 Claims, No Drawings

ISOMERIZATION OF ALKYL BENZENES USING A NU-1 ZEOLITE CATALYST

This is a division, of application Ser. No. 727,773 filed Sept. 29, 1976, now U.S. Pat. No. 4,060,590.

The present invention relates to a zeolite-like material hereinafter referred to as zeolite ν - 1, that is, nu-1, to a method of making it and to processes using it as a catalyst.

Zeolite nu-1 can be made from a synthesis mixture containing a silica source, an alumina source and a methylated quaternary ammonium compound and/or cationic degradation product thereof and/or mixtures, for example of trimethylamine and methanol, that produce a methylated quaternary ammonium compound; alternatively the corresponding phosphonium compounds can be used.

A considerable number of zeolite preparations involving the tetramethylammonium cation has already been described. These are surveyed in "Zeolite Molecular Sieves" by D. W. Breck (Wiley - Interscience 1974), pages 304 - 312, 348 - 378. The following is a list of what are believed to be the most pertinent examples, with references:

| | |
|---|---|
| N-A, N-X, N-Y | US 3306922 |
| ZK-4 | UK 1062879 |
| alpha | UK 1074130 |
| omega | UK 1178186 |
| TMA-O, TMA-E | Journal of the Chemical Society (London) 1970A, 1470-1475 |
| N | US 3414602 |
| ZSM-4 | UK patents 1117568, 1227294, 1297256, 1321460 and 1365318 |
| TMA-offretite | UK 1188043 |

Zeolite nu-1 is, however, shown by X-ray and other characterising information to be different from these and all other synthetic and natural zeolites. The X-ray data are presented hereinafter as a recorder chart (Example 13), a table of intensities derived from a recorder chart (Example 1), a table of intensities derived directly from diffraction measurements (Examples 8, 13, and 14) or the report of a comparison with a standard nu-1 chart. The data were determined using copper K alpha radiation.

We believe that the distinctive structure and properties of nu-1 result from exploration of synthesis at higher temperatures and higher water contents than have previously been used, with high silica to alumina ratios.

The invention provides zeolite nu-1 having a composition in the range 0.9 to 1.3 $R_2O \cdot Al_2O_3 \cdot$ 20 to 150 $SiO_2 \cdot$ 0 to 40 $H_2O$ where R is one or more of hydrogen, ammonium, phosphonium or 1/n of a cation of a metal of valency $n$ and having an X-ray diffraction pattern when R is H substantially as shown in Table 1.

This definition includes both freshly prepared zeolite nu-1 ("freshly prepared" means the product of synthesis and washing, with optional drying) and also forms of it resulting from dehydration and/or calcination and/or ion exchange. In freshly prepared nu-1 R is or includes ammonium or phosphonium selected from methylated quaternary ammonium and methylated quaternary phosphonium and cationic degradation products thereof (referred to hereinafter as Q) and may include an alkali metal, especially sodium. The freshly-prepared material may also contain quaternary compound trapped in the zeolite structure, but this does not constitute part of the composition for the purposes of the definition. The proportion of such compound is typically 0.5 to 2.5 mols of $Q_2O$ per $Al_2O_3$.

The silica to alumina ratio is preferably at least 40.

TABLE 1

| Zeolite nu-1 in hydrogen form | | | |
|---|---|---|---|
| d (A) | 100 I/Io | d (A) | 100 I/Io |
| 8.87 | 18 | 3.965 | 73 |
| 8.28 | 69 | 3.845 | 74 |
| 6.53 | 43 | 3.81 | 22 |
| 6.19 | 75 | 3.687 | 16 |
| 4.43 | 52 | 3.508 | 29 |
| 4.30 | 51 | 3.256 | 27 |
| 4.08 | 37 | 2.858 | 15 |
| 4.03 | 100 | | |

The $H_2O$ content of freshly prepared nu-1 depends on the conditions in which it has been dried after synthesis.

In calcined forms of nu-1, R may be alkali metal but includes less or no ammonium or phosphonium compound, since these are burnt out in the presence of air, leaving hydrogen as the balancing cation.

Among the ion-exchanged forms of nu-1 the ammonium ($NH_4^+$) is of importance since it can be readily converted to the hydrogen form by calcination. The hydrogen-form and forms containing metals introduced by ion exchange are described further below.

The data shown in Table 1 include estimated measurement errors and represent ranges of variation such as are common in the zeolite art as the result of impurities, of changes in the associated cations represented by R, and variations in detailed crystal structure within the scope of the essential nu-1 structure. In particular, the d-spacings in Table 1 may be up to 4% larger or 2% smaller, the zeolite may contain a combination of nu-1 forms from various parts of the d-spacing range, and in certain forms the 6.5 - 6.6 A line may be split into two. The accompanying drawing refers to the high d-spacing type with the split peak.

It will be noticed that the data in Table 1, which relates to the preparation described in Example 8, differ from those quoted in the provisional specifications filed on 3 October 1975 and 9 February 1976 in not including certain lines. Of these lines, that at d (A) 19.4 has since been identified with the impurity kenyaite and those at 6.17 and 3.19 as sodalite.

Zeolite nu-1 is characterised further by the following dye absorption properties:

| (a) | cationic dyes | |
|---|---|---|
| | acriflavine | nil |
| | phenosafranine | nil |
| | carbocyanine | very strong, purple or purple/blue |
| | methyl red | very strong |
| | toluylene red | nil |
| (b) | other dyes | |
| | alizarin | weak |
| | aurin | nil |
| | aluminon | nil without TMA |

The determination of these properties in comparison with other zeolites is described in Example 21 below.

Zeolite nu-1 is yet further characterised by its adsorption capacity for molecules of various sizes. The following % w/w adsorptive capacities at p/po = 0.5 were observed for the hydrogen nu-1 of Example 8, which is believed to be typical:

TABLE 2

| | |
|---|---|
| water 25° C | 6.8 |
| n - hexane 25° C | 2.7 |
| isobutane 25° C | 0.9 |
| p - xylene 25° C | nil in 2 hours |
| | 1.9 in 24 hours |

The slow adsorption of p - xylene suggest that nu-1 has internal spaces large enough to accommodate the p - xylene molecule, but that the entranceports to such spaces are small, probably about 6.0 A.

From Table 2 it is evident that zeolite nu-1 absorbs water to a greater extent than n- hexane by a factor of 1.5 to 4.0, based on weight percentages. Zeolite nu-1 is therefore to be considered as falling within the class of so-called "hydrophilic" zeolites, even though its silica to alumina ratio can be over 30 and thus at a level previously disclosed to be characterised by hydrophobic behaviour, that is, absorbing more n - hexane than water.

Whereas other characterising properties of nu-1 may yet be found, it is characterised particularly by its catalytic properties, in the hydrogen form, of high activity for xylenes isomerization and ethylbenzene conversion, with selectivity against xylenes disproportionation.

The invention provides also a method of making zeolite nu-1 by reacting an aqueous mixture comprising at least one silica source, at least one alumina source and at least one methylated quaternary ammonium or methylated quaternary phosphonium compound, the mixture having the molar composition $SiO_2/Al_2O_3$ — at least 10, preferably 20 to 200, especially 40 to 100

$Na_2O/SiO_2$ — 0 to 0.4, especially 0.05 to 0.25

$(Na_2O + Q_2O)/SiO_2$ — 0.1 to 6.0, preferably 0.1 to 5.0, especially 0.2 to 0.3

$H_2O/(Na_2O + Q_2O)$ — 5 to 500, especially 100 to 200

$Q_2O/(Na_2O + Q_2O)$ — 0.05 to 1.0, especially 0.4 to 0.7 where Q is methylated quaternary ammonium or methylated quaternary phosphonium $Na_2O$ and $Q_2O$ refer to free $Na_2O$ and $Q_2O$ only. The expressions "free $Na_2O$" and "free $Q_2O$" are generally understood in the zeolite art to denote hydroxides or salts of very weak acids such as aluminic or silicic acid such that such $Na_2O$ and $Q_2O$ are effective in the zeolite synthesis reaction. If waterglass is used as a silica source, the content of free $Na_2O$ and/or $Q_2O$ can be decreased to within the specified range by adding acid or adding alumina and/or Q in the form of a salt of a strong acid, for example as sulphate, nitrate or halide.

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fume silicas and silica gels suitably in grades for use as reinforcing pigments for rubber or silicone rubber. Colloidal silicas of various particle sizes may be used, for example 10 - 15 or 40 - 50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in UK Pat. No. 1,193,254, and silicates made by dissolving silica in alkali metal or quaternary mixture.

The alumina source is most conveniently sodium aluminate, but can be or include an aluminium an aluminium salt for example the chloride, nitrate or sulphate or alumina itself, which should preferably be in a hydrated or hydratable form such as colloidal alumina, pseudobohmite, bohmite, gamma alumina or the alpha or beta trihydrate.

In the reaction mixture for synthesising nu-1 at least part of the alumina can be provided in the form of one or more aluminosilicates.

The aluminosilicate compound provides preferably at least 20%, especially 50 - 100% of the alumina source. If the aluminosilicate compound contains sufficient silica, it can provide the whole of the silica source. However, since the silica to alumina ratio of zeolite nu-1 is much higher than that of readily available aluminosilicate compounds, the reaction mixture will normally contain a further silica source.

The aluminosilicate compound can be synthetic or naturally-occurring. If it is synthetic it can for example be a crystalline compound, such as a zeolite or an amorphous compound such as a gel or a zeolite precursor or a silica/alumina cracking catalyst. If it is naturally-occurring it may be for example a clay such as kaolin (especially in the form known as metakaolin made by calcination of kaolin at 500° - 950° C, especially 530° - 600° C), or one or more of attapulgite, dickite, halloysite, illite or montmorillonite. A naturally-occurring zeolite may be used if desired. Substances such as nepheline and kalsilite, which are available naturally or synthetically, can be used. In assembling the reaction mixture, account should be taken of other reactants introduced as part of the aluminosilicate material, such as water and alkali metal compounds; and preferably any interfering constituents such as compounds of Group II elements should be substantially absent. The aluminosilicate compound used can be one that has been made by treating with acid or with non-interfering cations the corresponding compound containing interfering cations. If desired, the aluminosilicate can have been de-aluminised by acid or chromium bleaching.

The use of aluminosilicate starting material makes possible a variant of the method in which such a material is introduced in shaped particulate form (especially as approximately spherical granules 1 - 10 mm in diameter of cylindrical compressed pellets or extrusions 2 - 10 mm in diameter and 5 - 20 mm in length) and the silica content, temperature and time are chosen so as to effect conversion to zeolite nu-1 only in the outer portions of those particles. By this method zeolite nu-1 can be obtained directly in shaped particles and the agglomeration procedures necessary for making such particles from powder are unnecessary. Typical conditions for such a variant of the method include $SiO_2 / Al_2O_3$ — 12 - 25 temperature — 150° - 200° C time — 1.5 to 3.0 days

The water content of the reaction mixture is preferably over 500, especially in the range 1000 to 4000 mols per mol of $Al_2O_3$.

The relative proportions of $Q_2O$ and $Na_2O$ can be chosen in relation to the intended sodium content of the zeolite produced, the sodium content and thus the need for ion-exchange being lower, the lower the proportion of $Na_2O$. The preferred range 0.4 to 0.7 is of general usefulness in giving a zeolite requiring a moderately intense ion exchange treatment, yet without the high cost of a high proportion of $Q_2O$.

The reaction should be continued preferably until the time when the zeolite product contains at least 50% w/w of nu-l. This time depends on the temperature and relative concentrations of reactants and on the whether the reaction mixture is quiescent or agitated. If the time of reaction is excessive, then zeolite nu-1 is converted into other products. The reaction is followed preferably by sampling the mixture and examining it at intervals. A typical reaction time is in the range 12 to 300 hours. The temperature is suitably in the range 80° – 300° C, preferably 135° – 280° and especially in the range 150° – 250° C.

In addition to the ingredients already mentioned, the reaction mixture can contain seed zeolite and/or a mineralising agent such as a nitrate, halide or sulphate of an alkali metal. Such an agent may be added as such or formed in situ by the reaction of an alkali metal hydroxide, aluminate or silicate with the appropriate acid or quaternary or aluminium salt.

At the end of the reaction, the solid phase is collected on a filter and washed and is then ready for further steps such as drying, dehydration and ion-exchange.

If the product of the reaction contains alkali metal ions, these have to be at least partly removed in order to prepare the hydrogen form of nu-1, and this can be done by ion exchange with an acid, especially a strong mineral acid such as hydrochloric acid or by way of the ammonium compound, made by ion exchange with a solution of an ammonium salt such as ammonium chloride. Such ion exchange can be carried out by slurrying once or several times with the solution. The zeolite is usually calcined after ion exchange and may be calcined before or between stages.

In general, the cation(s) of zeolite nu-1 can be replaced by any cation(s) of metals, and particularly by those in Groups IA, IB, IIA, IIB, III (including rare earths), VIIA (including manganese), VIII (including noble metals) and by lead and bismuth. (The Periodic Table is as in "Abridgments of Specifications" published by the UK Patent Office).

In order to prepare a catalyst zeolite nu-1 can be incorporated in an inorganic matrix, with other materials which can be either inert or catalytically active. The matrix may be present simply as a binding agent to hold the small zeolite particles (0.005 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica and kaolinic clays, bentonites, montmorillonites, sepiolite, attapulgite, Fullers earth, synthetic porous materials such as $SiO_2 Al_2O_3$, $SiO_2-ZrO_2$, $SiO_2-ThO_2$, $SiO_2-BeO$, $SiO_2-TiO_2$, or any combination of these oxides. An effective way of mixing zeolite nu-1 with such diluents is to mix appropriate aqueous slurries in a mixing nozzle and then to spray-dry the slurry. Other ways of mixing can be used.

If zeolite nu-1 in any cationic form or as a catalytic composite is exchanged or impregnated with hydrogenation/dehydrogenation components, such as Ni, Co, Pt, Pd, Re, Rh, hydrocracking and reforming catalysts can be made, especially if the $Na_2O$ content is less than 0.03% w/w.

A preferred hydrocarbon conversion process according to this invention comprises contacting a feed of an alkylbenzene or a mixture of alkylbenzenes under isomerisation conditions in the vapour or liquid phase with a catalyst comprising zeolite nu-1, especially in the preferred hydrogen form with a sodium oxide content of less than 0.15% w/w.

In the vapour phase, suitable isomerisation conditions include a temperature in the range 100° to 600° C, preferably 200° to 450° C and a pressure in the range 0.5 to 50, preferably 1 to 5, atmospheres absolute (ata).

In the liquid phase, suitable isomerisation conditions include a temperature in the range 0° to 350° C, a pressure in the range 1 to 200, preferably 5 to 70 ata and, in a flow system, a space velocity in the range 1 to 100, preferably 1 to 30 w/w hour, the higher flow rates being used at the higher temperatures. Optionally a diluent is present, suitably one or more of those having a critical temperature higher than the isomerisation temperature being used and including toluene, ethylbenzene, trimethylbenzene, naphthenes and paraffins. Preferably, the diluent if present, amounts to 1 to 90% by weight of the feed to the isomerisation reaction. In the above-mentioned processes the catalyst preferably contains no hydrogenation/dehydrogenation component.

Optionally the isomerisation reaction is conducted in the presence of hydrogen. A suitable mole ratio of hydrogen to alkylbenzene lies in the range 3 to 30:1. If hydrogen is used, it is preferred that the catalyst should comprise a metal of Group VIII of the Periodic Table together with the zeolite. Preferably the metal of Group VIII is platinum. The amount of metal used preferably lies in the range 0.1 to 2% by weight of metal based on the total weight of catalyst. If desired, the catalyst may contain one or more additional metals, for example rhenium, suitably in the range 0.1 to 2% by weight based on the total weight of catalyst.

Preferably the alkylbenzene is a xylene, for example m-xylene for conversion to p-xylene, or a mixture of xylenes, possibly with ethylbenzene. The amount of ethylbenzene present will depend to some extent on the source of the xylenes mixture but will usually lie in the range 0 to 25% by weight of the feedstock. In certain prior art xylenes isomerisation processes it is necessary to limit the amount of ethylbenzene in the feedstock to a relatively small amount, say less than 6% as above this level, the catalysts used cannot break down the ethylbenzene, which therefore tends to build up in recycle streams. The process of the invention is able to handle feedstocks containing relatively high (e.g. 6 – 25%) as well as relatively low amounts of ethylbenzene.

The isomerisation may be carried out in the presence of water vapour in a concentration of, for example 500 to 10,000 and preferably 1000 to 5000 parts per million by weight of the feedstock.

In the following Examples the ingredients had the following properties:
Silica AKZO KS 300 98.9% $SiO_2$ — 1.1% $Na_2O$
Sodium aluminate formula 1.25 $Na_2O . Al_2O_3$
"TMAOH" represents tetramethylammonium hydroxide and the solution used contained 25% w/w of TMAOH. metakaolin formula $Al_2O_3 . 2 SiO_2$; prepared by calcining kaolin in air for 17 hours at 550° C.

EXAMPLE 1

Preparation of Na - Q form of zeolite nu-1

For this preparation the synthesis mixture had the composition $Al_2O_3 \cdot 59.3\ SiO_2 \cdot 12.65\ Na_2O \cdot 10.76\ Q^+ \cdot 36.06\ OH^- \cdot 3580.3\ H_2O$. Solid silica (36 g of AKZO grade KS 300) was suspended in a mixture of 39.2 g of TMAOH solution and 500 g water. Next 1.8 g solid sodium aluminate and 8.6 g solid sodium hydroxide were dissolved in 115 g water and stirred into the silica suspension (10 minutes). The resulting slurry was heated for 8 days at 170° C in a 1 liter Pyrex (R.T.M.) liner in a 5 liter autoclave without agitation. After cooling to about 60° C, the slurry was filtered and washed with 500 mls hot water, and dried at 120° C. The product, zeolite nu-1, had the X-ray diffraction data shown in Table 3 and the composition $0.7\ Na_2O \cdot 0.3\ Q_2O \cdot Al_2O_3 \cdot SiO_2 \cdot 6\ H_2O$ where Q is tetramethyl ammonium, and a crystallite size of about 5 microns.

This product was calcined in air overnight at 550° C and was found to have substantially the same X-ray diffraction pattern as the hydrated tetramethylammonium-containing zeolite nu-1.

TABLE 3

X-ray diffraction data = freshly prepared nu-1 (Example 1)

| | d(A) | 100 I/Io | d(A) | 100 I/Io |
|---|---|---|---|---|
| K | 19.4 | 2.5 | 4.01 | 100 |
| | 11.33 | 2.5 | 3.95 | 38 |
| | 8.80 | 8.0 | 3.83 | 62 |
| | 8.23 | 41 | 3.51 | 35 |
| | 6.94 | 2.5 | 3.42 | 24 |
| | 6.49 | 32 | 3.24 | 11 |
| S-1 | 6.17 | 55 | S 3.19 | 11 |
| | 5.61 | 11 | 3.08 | 11 |
| | 5.34 | 10 | 2.98 | 11 |
| | 4.41 | 46 | 2.94 | 5 |
| | 4.28 | 49 | 2.85 | 8 |
| | | | 2.76 | 8 |
| | | | 2.73 | 4 |
| | | | 2.67 | 10 |

Notes:
K denotes a line identified as Kenyaite
S denotes lines identified as sodalite
S-1 denotes a nu-1 line reinforced by a neighboring sodalite line

EXAMPLE 2

Preparation of hydrogen form of nu-1

The calcined product of Example 1 was slurry-exchanged three times with its own weight of 10% ammonium chloride solution at 25° C for 1 hour for each exchange stage. The product was calcined in air overnight at 550° C, and was found to have substantially the same X-ray diffraction pattern as the zeolite nu-1 originally made in Example 1, a crystallite size of about 5 μ, and the composition:

$$0.01\ Na_2O \cdot Al_2O_3 \cdot 55\ SiO_2$$

This hydrogen nu-1 zeolite had a water adsorptive capacity of 3.5% w/w (p/po = 0.7, 25° C), and adsorbed 3% w/w n hexane (p/po = 0.6 25° C). It did not significantly adsorb p-xylene. These results suggest a window size of at least 5A, but less than 6A.

EXAMPLE 3

Isomerisation of xylenes

The hydrogen zeolite nu-1 of Example 2 was employed as a catalyst in the isomerisation of xylene mixtures containing only 7% p-xylene and 11% ethylbenzene. It was found that the catalyst exhibited very low decay rates, and gave virtually complete and very advantageous conversion of ethylbenzene to diethylbenzene; it also gave very low xylene loss. The p-xylene lift to equilibrium levels on zeolite nu-1 was obtained at a temperature 200° C lower than on $SiO_2/Al_2O_3$ xylene isomerisation catalyst.

EXAMPLE 4

Preparation using mixture of lower sodium content 0.9 g sodium aluminate powder and 2.2 g sodium hydroxide pellets were dissolved in 300 ml water. 29.4 g of TMAOH solution were added to this solution and 18 g fine silica stirred into it. The resulting suspension was stirred for 1 hour at 60° C and then maintained at 170° C in an autoclave for 6½ days. The reaction mixture thus had a composition with molar ratios as follows: $SiO_2/Al_2O_3 = 60$; $Na_2O/SiO_2 = 0.11$; $(Na_2O + Q_2O)/SiO_2 = 0.25$; $H_2O/(Na_2O + Q_2O) = 230$; $Q_2O/(Na_2O + Q_2O) = 0.57$ where Q is tetramethylammonium. The mixture after cooling to room temperature was filtered, washed with water, and dried in air at 120°. The resulting finely divided solid was slurry-exchanged by suspension in a solution of 20 g ammonium chloride in 300 ml water at 50° for 0.5 hour. The zeolite formed was filtered off and washed with water. At this stage the sodium content of the zeolite was 0.14% Na, by weight. The material was then calcined at 500° C for 16 hours. Three further treatments with the ammonium chloride solution reduced the sodium content to 0.08% Na.

EXAMPLE 5

Xylenes isomerisation

Pellets consisting of 67% zeolite in the hydrogen form prepared as described in Example 4 and 33% pseudobőhmite alumina (25% water) were prepared. 7 g of pellets were placed in a laboratory-size reactor for xylenes isomerisation. A feed of mixed xylenes (composition as shown in Table 4) was passed over the catalyst at flows varying from 10cc to 15cc per hour. Three runs totalling 24 hours each were made at 450° C and during each run the catalyst showed no loss of activity. At the end of each run, examination of the catalyst revealed only very slight evidence of carbon lay-down on the catalyst. The feed composition and product composition in the three runs are shown in Table 4.

TABLE 4

| | Composition of Feed (Wt%) | Composition of Product | | |
|---|---|---|---|---|
| | | Run 1 | Run 2 | Run 3 |
| Benzene | 0.05 | 0.90 | 0.71 | 0.69 |
| Toluene | 0.27 | 0.74 | 0.58 | 0.60 |
| Ethylbenzene | 5.80 | 4.53 | 4.64 | 4.77 |
| Paraxylene | 8.38 | 18.92 | 17.94 | 17.57 |
| Metaxylene | 54.77 | 47.94 | 48.47 | 48.65 |
| Orthoxylene | 29.30 | 25.94 | 26.43 | 26.54 |
| Aromatic $C_9$'s | 0.3 | — | 0.53 | — |
| Aromatic $C_{10}$'s | 0.05 | — | 0.05 | — |
| n-$C_9$ paraffin | 1.20 | undeterm'd | 0.75 | undeterm'd |

The xylenes loss by disproportionation in each run was about 0.7%, based on the toluene formed. In conventional isomerisation processes using silica/alumina catalysts, a loss of about 2% usually occurs and the activity of such catalysts usually declines in similar experiments.

EXAMPLE 6

The process described in Example 5 was repeated using the same catalyst and under the same conditions except that the feed contained a relatively large amount of ethyl benzene. The feed composition and product composition in 2 runs are shown in Table 5.

TABLE 5

| | Composition of Feed (wt%) | Composition of Product Run 1 | Run 2 |
|---|---|---|---|
| Benzene | — | 1.31 | 1.42 |
| Toluene | 0.27 | 0.59 | 0.60 |
| n-nonane | 1.35 | 1.09 | 1.16 |
| Ethylbenzene | 12.20 | 9.46 | 9.42 |
| Para-xylene | 7.58 | 16.52 | 16.47 |
| Meta-xylene | 51.27 | 46.18 | 46.07 |
| Ortho-xylene | 27.34 | 24.18 | 24.86 |
| Aromatic $C_9$ | 0.34 | | |
| Aromatic $C_{10}$ | 0.05 | | |

This example shows that the catalyst comprising nu-1 zeolite is able to handle a feedstock containing a relatively large amount of ethylbenzene, the latter being cracked to form benzene.

The activity and selectivity of the hydrogen form of zeolite nu-1 of Example 4 were better than those of the sample prepared in Example 2. The reasons for this are not altogether clear but it is believed that among the factors playing a part may be the following:

(a) the smaller crystallite size of the Example 4 zeolite, most of the crystallites being less than 1 μ in size.
(b) the relatively low sodium content of the Example 4 zeolite.
(c) the modified method of preparation; (i) whereas in Examples 1 and 2 the zeolite was washed, dried at 120°, calcined at 550° C, slurry-exchanged with ammonium chloride solution and then again calcined, in Example 4 calcination was carried out only after the slurry-exchange with ammonium chloride; and (ii) in the reaction mixture a rather higher ratio $Q_2O/Na_2O$ was used than in Example 1.

EXAMPLE 7

Example 1 was repeated subject to the modification that the synthesis was carried out under 20 ata pressure of nitrogen and without agitation, so as to ensure quiescent conditions. The product had the composition $$0.7\ Na_2O\ .\ 2.3\ Q_2O\ .\ Al_2O_3\ .\ 52\ SiO_2\ .\ 10.5\ H_2O$$

of which about 2.0 molecules of $Q_2O$ are non-structural and a crystallite size of 3 to 5 microns. Its X-ray diffraction pattern was typical of zeolite nu-1.

EXAMPLE 8

Preparation of hydrogen form of nu-1

The product of Example 7 (1.3% w/w $Na_2O$) was mixed with 2 ml of 5% w/w hydrochloric acid per gram of product. The mixture was boiled under reflux for 5 hours, then filtered and washed with demineralised water. The washed product (0.3% w/w $Na_2O$) was re-slurried with 60 ml of 0.365% w/w hydrochloric acid per gram of solid, held at 50° C for 1 hour, then filtered, washed with demineralised water and dried. The dried product contained 0.019% w/w $Na_2O$. It was then calcined at 450° C overnight to effect controlled burn-off of its content of tetramethylammonium without excessive temperature rise. The calcined product had the composition $$0.01\ Na_2O\ .\ Al_2O_3\ .\ 50\ SiO_2$$

Its % w/w adsorption capacity for water and n-hexane was measured at 25° C, p/po 0.5, with the following results:
water — 6.8
isobutane — 0.9
n-hexane — 2.7
p xylene — nil after 2 hours, 1.9 after 24 hours
These adsorption data suggest that ports into the zeolite structure are of diameter not over 6.0 A.

The X-ray diffraction data for this hydrogen nu-1 are set out in Table 6.

When tested as in Examples 5 and 6, this zeolite sample was more active and selective than that of Example 4.

TABLE 6

| d (A) | Est. error | 100 I/Io | d (A) | Est. error | 100 I/Io | d (A) | Est. error | 100 I/Io |
|---|---|---|---|---|---|---|---|---|
| 11.45 | 0.04 | 4 | 3.76 | 0.01 | ~4 | 2.612 | 0.005 | 3 b |
| 8.87 | 0.03 | 18 | 3.687 | 0.005 | 16 | 2.574 | 0.005 | 1 s |
| 8.28 | 0.02 | 69 | 3.645 | 0.004 | 13 s | 2.523 | 0.005 | ~1 |
| 6.53 | 0.02 | 43 | 3.508 | 0.004 | 29 b | 2.503 | 0.004 | 4 |
| 6.31 | 0.03 | ~11 s ⎫ | 3.430 | 0.005 | 8 | 2.488 | 0.004 | 5 |
| 6.19 | 0.02 | 75 ⎭ | 3.387 | 0.008 | ~1 | 2.471 | 0.003 | 6 |
| 5.74 | 0.02 | 3 | 3.256 | 0.004 | 27 b | 2.448 | 0.003 | ~1 |
| 5.63 | 0.02 | 11 b | 3.15 | 0.01 | 2 s | 2.436 | 0.003 | 4 |
| 5.36 | 0.01 | 10 | 3.087 | 0.005 | 13 b | 2.40 | 0.01 | 1 b |
| 4.61 | 0.01 | 10 | 2.998 | 0.004 | 11 b | 2.345 | 0.003 | 2 |
| 4.43 | 0.01 | 52 | 2.948 | 0.006 | 7 | 2.325 | 0.005 | 4 b |
| 4.30 | 0.01 | 51 | 2.912 | 0.004 | 10 ⎫ | 2.300 | 0.002 | 5 |
| 4.15 | 0.02 | ~2 ⎫ | 2.876 | 0.005 | 11 ⎬ | 2.253 | 0.002 | 1 |
| 4.08 | 0.02 | ~37 ⎬ | 2.858 | 0.004 | 15 ⎭ | | | |
| 4.03 | 0.01 | 100 ⎭ | 2.823 | 0.004 | 7 | | | |
| 3.965 | 0.005 | 73 ⎫ | 2.773 | 0.005 | 10 b | | | |
| 3.94 | 0.01 | shoulder ⎭ | 2.748 | 0.003 | 12 b | | | |
| 3.845 | 0.005 | 74 ⎫ | 2.671 | 0.004 | 10 b | | | |
| 3.81 | 0.01 | ~22 ⎭ | 2.630 | 0.003 | 2 | | | |

~ = approximately
s = lines due to sodalite type impurity
b = broad line
⎭ = incompletely resolved lines

EXAMPLE 9

Preparation on a larger scale

Example 7 was repeated with the modification that the scale was on the basis of 46.4 g of the sodium aluminate (0.26 mol of $Al_2O_3$) and that synthesis was carried out at 180° C for 3 days in a "Pyrex" (R.T.M.)-lined 25 liter autoclave. The product was found by X-ray diffraction to be very similar to that of Example 7. Its composition, after drying at 120° C, was $$0.06\ Na_2O\ .\ 2.2\ Q_2O\ .\ Al_2O_3\ .\ 49.9\ SiO_2\ .\ 8.9\ H_2O$$

Of the 2.2 $Q_2O$ about 1.1 molecules are loosely bound, leaving 1.1 molecules forming part of the zeolite structure.

EXAMPLE 10

Preparation using more concentrated synthesis mixtures

Example 1 was repeated using 25% less water and with a synthesis time of 6 days at 180° C, in a 5 liter "Pyrex" (R.T.M.)-lined autoclave without agitation and without gas under pressure. The product after drying at 120° C had the composition $$0.34\ Na_2O\ .\ 1.9\ Q_2O\ .\ Al_2O_3\ .\ 40\ SiO_2\ .\ 9.2\ H_2O$$

of which 1.1 molecules of $Q_2O$ are non-structural. Its X-ray diffraction pattern was of the low d-spacing type similar to the product of Example 7.

EXAMPLE 11

Preparation at lower sodium content and higher concentration

A mixture having the composition $$1.89\ Na_2O\ .\ 13.75\ Q_2O\ .\ Al_2O_3\ .\ 59.3\ SiO_2\ .\ 1930\ H_2O$$

was reacted on the scale of 3.3 g of sodium aluminate (0.018 mol $Al_2O_3$) was reacted quiescently in a "Pyrex" (R.T.M.)-lined 5 liter autoclave under 80 ata nitrogen pressure at 170° C for 8 days. The solid phase was collected on a filter, washed, dried at 120° C, and then had the composition $$0.11\ Na_2O\ .\ 1.6\ Q_2O\ .\ Al_2O_3\ .\ 66\ SiO_2\ .\ 7\ H_2O$$

of which 0.6 molecule of $Q_2O$ is non-structural.

Its X-ray diffraction pattern differed from that of Table 1 in having doubled main peaks, suggesting that it consisted of a mixture of low $d$ and high $d$ material.

EXAMPLE 12

Example was repeated subject to the modifications that the synthesis was carried out in a 1 liter stainless steel autoclave with stirring at 500 rpm. Samples were taken at intervals and examined by X-ray diffraction. From 17 hours to 89 hours reaction time, at which the synthesis was voluntarily stopped, the solid phase contained zeolite nu-1 as its sole crystalline constituent. Its X-ray diffraction pattern was substantially the same as that of Example 11, except the peak at 6.6 A was split.

EXAMPLE 13

Synthesis mixtures of very low sodium content (a) A reaction mixture of composition $$0.64\ Na_2O\ .\ 5.4\ Q_2O\ .\ Al_2O_3\ .\ 59.3\ SiO_2\ .\ 1059\ H_2O$$

was prepared using as alumina source 6.2 g of pseudo-böhmite containing 200 ppm of $Na_2O$ and introducing it by dissolving it in TMAOH solution at 60° for 1 hour. It was then reacted in a 1 liter stainless steel autoclave at 180° C for 24 hours with agitation. The product after washing and drying at 120° C overnight had the composition $$0.09\ Na_2O\ .\ 2.9\ Q_2O\ .\ Al_2O_3\ .\ 47.8\ SiO_2\ .\ 4.1\ H_2O$$

of which 1.9 molecules of $Q_2O$ are non-structural.

Its X-ray diffraction pattern was as shown in Table 7 and the accompanying drawing. The $d$ spacings are about 1% higher than in Table 1 and two peaks occur at 6.5–6.6 A.

(b) A reaction mixture of composition $$0.008\ Na_2O\ .\ 5.4\ Q_2O\ .\ Al_2O_3\ .\ 60\ SiO_2\ .\ 945\ H_2O$$

was prepared as in (a), but using ingredients selected to introduce still less sodium. After a synthesis time of 48 hours but otherwise in the condition of (a) the product had the composition and X-ray diffraction pattern similar to (a).

It is thus possible to produce zeolite nu-1 directly in a substantially sodium-free form, convertible to the hydrogen form without ion exchange.

TABLE 7

| d (A) | Est. error | 100 I/Io | d (A) | Est. error | 100 I/Io | d (A) | Est error | 100 I/Io |
|---|---|---|---|---|---|---|---|---|
| 11.56 | 0.06 | 2 | 3.906 | 0.005 | 86 | 2.893 | 0.003 | 7 |
| 8.97 | 0.03 | 26 | 3.842 | 0.005 | 34 ) | 2.794 | 0.003 | 14 |
| 8.33 | 0.02 | 62 | 3.819 | 0.008 | ~9 ) | 2.766 | 0.003 | 17 ) |
| 6.60 | 0.02 | 27 | 3.713 | 0.004 | 21 | 2.710 | 0.003 | 10 ) |
| 6.54 | 0.02 | 27 | 3.562 | 0.004 | 43 | 2.693 | 0.003 | 4 ) |
| 6.26 | 0.02 | 72 | 3.468 | 0.007 | ~1 ) | 2.635 | 0.002 | 4 ) |
| 5.86 | 0.03 | 1 | 3.441 | 0.004 | 6 ) | 2.552 | 0.005 | 1 |
| 5.765 | 0.02 | 3 | 3.305 | 0.004 | 17 | 2.532 | 0.002 | 3 |
| 5.675 | 0.02 | 9 ) | 3.261 | 0.004 | 22 | 2.506 | 0.002 | 5 |
| 5.65 | 0.02 | 9 ) | 3.209 | 0.006 | 1 | 2.487 | 0.002 | 7 |
| 5.39 | 0.01 | 11 | 3.147 | 0.004 | ~5 ) | 2.449 | 0.002 | 5 ) |
| 4.642 | 0.007 | 11 | 3.125 | 0.003 | 21 ) | 2.421 | 0.004 | ~1 ) |
| 4.476 | 0.007 | 67 | 3.064 | 0.005 | 3 | 2.408 | 0.004 | 2 ) |
| 4.324 | 0.006 | 62 | 3.021 | 0.004 | 8 ) | 2.349 | 0.004 | 3 ) |
| 4.161 | 0.008 | ~6 | 3.007 | 0.004 | 8 ) | 2.339 | 0.004 | 5 ) |
| 4.101 | 0.006 | 47 | 2.981 | 0.003 | 10 | 2.321 | 0.002 | 8 |
| 4.047 | 0.007 | 100 | 2.949 | 0.003 | 11 | 2.304 | 0.004 | 1 |
| 4.010 | 0.005 | 37 | 2.897 | 0.006 | ~5 ) | 2.285 | 0.002 | 2 |
| 3.969 | 0.005 | 47 | 2.881 | 0.004 | 19 ) | 2.269 | 0.002 | 1 |

~ = approximately

) = incompletely resolved lines

EXAMPLE 14

A reaction mixture similar to that of Example 1 and having the composition 11.7 Na$_2$O . 5.2 Q$_2$O . Al$_2$O$_3$ . 60.5 SiO$_2$ . 37.83 H$_2$O was reacted quiescently for 1 day at 230° C under autogenous pressure. The solid phase, after washing and drying contained alpha-quartz as impurity and a nu-1 component having inter alia the following lines in its X-ray diffraction pattern:

TABLE 8

| d A | 100 I/Io |
|---|---|
| 8.98 | 17 |
| 8.39 | 55 |
| 6.60 | 39 |
| 6.27 | 57 |
| 4.48 | 53 |
| 4.34 | 48 |
| 4.13 | 41 |
| 4.07 | 100 |
| 4.01 | 62 |
| 3.995 | |
| 3.896 | 74 |
| 3.555 | 26 |
| 3.294 | 32 |

Comparison with the patterns for Examples 1 and 8 shows that this is an example of the high d spacing type of zeolite nu-1.

EXAMPLE 15

Synthesis at higher temperature

Example 7 was repeated with the modification that the mixture was reacted at 250° C for 24 hours. The product was nu-1 of the high d spacing type similar to that of Example 14.

EXAMPLE 16

Synthesis with and without seed

Three synthesis runs were carried out using a reaction mixture having the molar composition 5.4 Na$_2$O . 5.6 Q$_2$O . Al$_2$O$_3$ . 55.6 SiO$_2$ . 3327 H$_2$O In each run sodium aluminate (2.4 g) sodium hydroxide (3.8 g) and TMAOH (54 g of solution) were dissolved in 300 g water and the resulting solution was stirred into a suspension of silica KS 300 (45 g) in 458 g water.

(a) To one mixture were added 4.5 g of zeolite nu-1 of the low d spacing type made in Example 10 above. The resulting seeded mixture was heated at 180° C for 24 hours. The solid phase was collected on a filter, washed and dried. Its X-ray diffraction pattern was substantially the same as that of the product of Example 14, that is, a high d spacing split peak variant of zeolite nu-1.

(b) The second mixture was heated at 180° C without any addition of seed zeolite. Conversion to zeolite nu-1 took 72 hours. Its X-ray diffraction pattern was substantially the same as that of the product of Example 14, that is, a split peak variant of zeolite nu-1.

(c) The third mixture was seeded with 2.5 g of zeolite nu-1 of the split peak type produced in Example 13. Its X-ray diffraction pattern was the same as that of the seed zeolite.

EXAMPLE 17

Zeolite nu-1 with higher silica to alumina ratio a synthesis mixture of composition 3.74 Na$_2$O . 17 Q$_2$O . Al$_2$O$_3$ . 120 SiO$_2$ . 3527 H$_2$O was made up be dissolving sodium aluminate (1.8 g), sodium hydroxide (2 g) TMAOH (124 g of solution) in 200 g water and stirring the resulting solution into a suspension of silica KS 300 (72 g) in 340 g water. The mixture was reacted in a 1 liter "Pyrex" (R.T.M.)-lined in a 5 liter rocking autoclave under 20 ata nitrogen pressure at 170° C for 3 days. The solid phase was collected on a filter, washed and dried. It had the composition 0.1 Na$_2$O . 2.2 Q$_2$O . Al$_2$O$_3$ 120 SiO$_2$ . 4.3 H$_2$O Its X-ray diffraction pattern was substantially the same as that of the product of Example 12, that is, the multiple-peak variant of zeolite nu-1.

EXAMPLE 18

The reaction mixture was as shown in Table 9. The sodium hydroxide was dissolved in the mixture of TMAOH solution and water. The silica and metakaolin were dispersed in the resulting mixture with vigorous stirring. The slurry was then reacted quiescently for 8 days at 180° C in a "Pyrex" (R.T.M.)-lined autoclave in the presence of gaseous nitrogen at 20 ata pressure, then let-down and cooled to almost 60° C. The solid phase was collected on a filter, washed with 1 liter of hot water, dried for 17 hours at 80° C and examined for chemical composition and by X-ray diffraction. Its composition was 0.7 Na$_2$O . 2.1 Q$_2$O . Al$_2$O$_3$ . 55 SiO$_2$ . 7 H$_2$O and its X-ray diffraction pattern was substantially the same as that of low d spacing type nu-1 zeolite.

TABLE 9

| Ingredient | Molar Contribution | | | | | |
|---|---|---|---|---|---|---|
| | Al$_2$O$_3$ | SiO$_2$ | Na$_2$O | Q$^+$ | OH$^-$ | H$_2$O |
| Silica KS 300 18 g | | 0.294 | 0.0032 | | 0.0064 | |
| TMAOH 19.6 g | | | | 0.0538 | 0.0538 | 0.816 |
| Water 306 g | | | | | | 17.0 |
| Metakaolin 1.1 g | 0.005 | 0.01 | | | | |
| Sodium hydroxide 4.8 g | | | 0.06 | | 0.12 | |
| | 0.005 | 0.304 | 0.0632 | 0.0583 | 0.1802 | 17.816 |
| per Al$_2$O$_3$ | 1.0 | 60.8 | 12.64 | 10.76 | 36.04 | 3563.2 |

EXAMPLE 19

The reaction mixture was as shown in Table 10. The procedure was the same as in Example 18, except that the reaction time was 3 days and the reaction was carried out in a rocking autoclave with glass lining. During the reaction the silica/alumina beads broke down giving a finely divided solid phase. The product zeolite had the composition $$0.3\ Na_2O \cdot 1.9\ Q_2O \cdot Al_2O_3 \cdot 52\ SiO_2 \cdot 10\ H_2O$$

and its X-ray diffraction pattern was substantially the same as that of the low $d$ spacing type of nu-1 zeolite.

TABLE 10

| Ingredient | Molar Contributon | | | | | |
|---|---|---|---|---|---|---|
| | $Al_2O_3$ | $SiO_2$ | $Na_2O$ | $Q^+$ | $OH^-$ | $H_2O$ |
| Silica sol 459 g | | 2.3 | | | | 17.85 |
| Sodium hydroxide 36.7g | | | 0.46 | | 0.92 | |
| TMA 25% w/w aq. 180.6g | | | | 0.496 | 0.496 | 7.53 |
| Silica/alumina 32.3g cracking catalyst (1 mm beads) | 0.046 | 0.46 | | | | |
| Water 60.8 g | | | | | | 3.67 |
| | 0.046 | 2.76 | 0.46 | 0.496 | 1.416 | 29.05 |
| per $Al_2O_3$ | 1.0 | 60 | 10 | 10.8 | 30.78 | 631.5 |

EXAMPLE 20

The reaction mixture was as shown in Table 11. The time was 2 days, a rocking autoclave was used and its lining was made of "Pyrex" (R.T.M.) The solid phase resulting from this reaction was in bead form. Incomplete formation of zeolite nu-1 had taken place as a result of the low silica content and alkalinity of the reaction mixture and short reaction time. The zeolite product had the chemical composition $$0.9\ Na_2O \cdot 1.5\ Q_2O \cdot Al_2O_3 \cdot 40\ SiO_2 \cdot 15\ H_2O$$

and an X-ray diffraction pattern characteristic of zeolite nu-1.

TABLE 11

| Ingredient | Molar Contribution | | | | | |
|---|---|---|---|---|---|---|
| | $Al_2O_3$ | $SiO_2$ | $Na_2O$ | $Q^+$ | $OH^-$ | $H_2O$ |
| Waterglass 59.3 g | | 0.27 | 0.135 | | 0.27 | 1.93 |
| TMAOH solution 59 g | | | | 0.16 | 0.16 | 2.46 |
| Silica/alumina 37.9g cracking catalyst | 0.054 | 0.54 | | | | |
| Water 575 g | | | | | | 31.9 |
| | 0.054 | 0.81 | 0.135 | 0.16 | 0.43 | 36.29 |
| per $Al_2O_3$ | 1.0 | 15 | 2.5 | 2.96 | 7.96 | 672 |

EXAMPLE 21

Dye adsorption properties

The dye adsorption properties of zeolite nu-1 in two forms, A-hydrogen form containing TMA and B-hydrogen form without TMA, were compared with those of zeolites Y, ZSM 5 and mordenite, each in hydrogen form, by adding 0.2 g of the zeolite to 5 ml of a saturated aqueous solution of the dye, shaking for 5 minutes, allowing to stand overnight, filtering, washing thoroughly and observing the extent of coloration of the zeolite. The adsorption of dyes containing cation groups is shown in Table 12.

TABLE 12

| Zeolite | DYE | | | | |
|---|---|---|---|---|---|
| | Acriflavine | Carbocyanine | Methyl Red | Pheno-Safranine | Toluylene Red |
| nu-1(TMA) | nil | very strong: purple | very strong | NA | NA |
| nu-1 (no TMA) | nil | very strong: purple/blue | very strong | nil | nil |
| Y | medium | nil | nil | nil | nil |
| ZSM 5 | very strong | very strong: blue | very strong | very strong | very strong |
| mordenite | very strong | very strong: blue | nil | nil | nil |

The adsorption of dyes not containing cation groups is shown in Table 13.

TABLE 13

| Zeolite | DYE | | |
|---|---|---|---|
| | Alizarin | Aurin | Aluminon C.I. 724 |
| nu-1 (TMA) | very strong | nil | NA |
| nu-1 (no TMA) | very strong | medium | nil |
| Y | nil | nil | nil |
| ZSM 5 | nil | very strong | very strong |
| mordenite | weak | medium | very strong |

We claim:

1. A process for the isomerisation of alkyl benzenes which comprises contacting a feed of an alkyl benzene or a mixture of alkyl benzenes under isomerisation conditions in the liquid or vapour phase with a catalyst comprising zeolite nu-1 having a composition expressed by the formula $$0.9\ to\ 1.3\ R_2O \cdot Al_2O_3 \cdot 20\ to\ 150\ SiO_2 \cdot 0\ to\ 40\ H_2O$$

where R is one or more of hydrogen, ammonium, phosphonium or $1/n$ of a cation having a valency $n$ and having a X-ray diffraction pattern when R is H substantially as shown in Table 1.

2. A process according to claim 1 in which the reactants are present in the vapour phase, added free hydrogen is substantially absent, the temperature is in the range 200°–450° C, the pressure in the range 1 to 5 ata and the catalyst contains substantially no hydrogenation/dehydrogenation components.

3. A process according to claim 2 in which the starting materials include xylenes and ethylbenzene and the process conditions are chosen so that ethylbenzene is converted.

* * * * *